United States Patent [19]
Copeland, Jr.

[11] Patent Number: 5,389,346
[45] Date of Patent: Feb. 14, 1995

[54] BIO-HAZARDOUS WASTE COMPACTOR

[76] Inventor: Maxie L. Copeland, Jr., Rte. 3, Box 278, Rayville, La. 71269

[21] Appl. No.: 123,706

[22] Filed: Sep. 20, 1993

Related U.S. Application Data

[63] Continuation of Ser. No. 853,148, Mar. 18, 1992, abandoned.

[51] Int. Cl.6 .................................................. B30B 9/00
[52] U.S. Cl. ............................... 422/292; 100/90; 100/99; 100/131; 100/229 A; 422/297; 422/300; 422/302
[58] Field of Search ............... 422/292, 297, 299, 300, 422/302, 24; 100/90, 70 R, 229 A, 131, 100, 99; 241/606, 199.11; 383/109, 113; 220/403, 404; 588/210, 212, 900; 423/DIG. 18, DIG. 20

[56] References Cited

U.S. PATENT DOCUMENTS

| | | | |
|---|---|---|---|
| 556,482 | 3/1896 | Swanson | 100/226 |
| 3,589,277 | 6/1971 | Gray et al. | 100/95 |
| 3,756,150 | 9/1973 | Bourgeois | 100/229 A |
| 3,822,037 | 7/1974 | Long | 220/403 |
| 3,831,514 | 8/1974 | Jernstrom | 100/70 |
| 3,881,408 | 5/1975 | Valor | 100/229 A |
| 3,941,046 | 3/1976 | Smith | 100/45 |
| 4,008,658 | 2/1977 | Stock et al. | 100/53 |
| 4,036,152 | 7/1977 | Bright | 110/191 |
| 4,073,229 | 2/1978 | O'Rourke et al. | 100/229 A |
| 4,184,825 | 1/1980 | Wolf | 425/85 |
| 4,273,037 | 6/1981 | Ruebesam | 100/91 |
| 4,374,491 | 2/1983 | Stortroen et al. | 422/26 |
| 4,407,191 | 10/1983 | Brenner | 100/99 |
| 4,423,987 | 1/1984 | Powers | 141/104 |
| 4,483,248 | 11/1984 | Ostreng | 100/99 |
| 4,735,136 | 4/1988 | Lee et al. | 100/229 A |
| 4,781,111 | 11/1988 | Chesnut | 100/229 A |
| 4,890,936 | 1/1990 | Cooper | 383/109 |
| 4,989,506 | 2/1991 | McCormick | 100/90 |
| 5,012,732 | 5/1991 | Fox | 100/35 |
| 5,078,508 | 1/1992 | Johan et al. | 383/109 |
| 5,129,735 | 7/1992 | Neal et al. | 220/404 |

OTHER PUBLICATIONS

Stanley N. Pinder, P. E., "Incineration of Predensified Hospital Waste", Custom Waste Management Corporation, Mar. 1989.

Primary Examiner—W. Gary Jones
Assistant Examiner—Laura E. Collins
Attorney, Agent, or Firm—Ronald P. Kananen

[57] ABSTRACT

A bio-hazardous waste compactor is described which provides a negative air pressure and venting system while allowing for the filtration of the air and control of sound. The compactor contains a sealed chamber which includes a sump area in the bottom of the chamber for fluid control. Waste is weighed so that the operator knows when to remove the waste. Ultraviolet light is provided to prevent the growth of vegetative pathogenic organisms. Finally, a disposable bag to be used in connection with such a bio-hazardous waste compactor is described which has an inner porous layer, an intermediate, biocide-containing, super-absorbent polymer layer and an outer non-porous layer.

22 Claims, 4 Drawing Sheets

BIO-HAZARDOUS WASTE COMPACTOR

This application is a continuation of application Ser. No. 07/853,148 filed Mar. 18, 1992, now abandoned.

FIELD OF THE INVENTION

This invention relates to an apparatus for use in medical facilities where bio-hazardous waste is collected in large volumes and must be disposed of in a safe, sanitary, and economical fashion. More particularly, this invention relates to an apparatus adapted to compact bio-hazardous waste consisting of solid, semisolid, and small amounts of liquid waste, while ensuring that such waste is sealed within the apparatus.

BACKGROUND OF THE INVENTION

In the past, most bio-hazardous waste was burned in incinerators owned by a hospital or other medical facilities. Due to current laws, a large number of rural areas cannot operate an incinerator because of the expense of maintaining the incinerator in compliance with current regulations. Rural hospitals and clinics must, therefore, contract with a waste disposal company to dispose of their bio-hazardous waste. These companies usually charge a lump sum amount per box with a maximum weight allowed. Thus the medical facility is not able to pack each box to its maximum weight. On the other hand, attempting to compact the material by hand is unsafe.

Trash compactors are available in the prior art which attempt in some way to filter airborne contaminants produced by the trash during compaction. For example, U.S. Pat. No. 4,008,658 to Stock et al. describes an apparatus for compacting waste material such as paper, fabrics, plastics, light metal, and so forth. In order to capture particles of dust, such as radiation-contaminated particles generated during receiving and hydraulic compacting operations, the apparatus is provided with a removable drum, a loading chamber over the drum and an exhaust system communicated with the loading chamber to draw off and filter particles of dust and other contaminants. The atmosphere in the chamber that is evacuated is replaced by an atmosphere that is drawn in around the sides of the drum.

U.S. Pat. No. 4,273,037 to Ruebesam describes a hydraulic trash compactor for low-level radiation applications wherein dust produced during trash compaction is removed from the compactor and filtered. The trash compactor has a base frame with vertical I-beam piston guide means supporting a rectangular piston for vertical reciprocation. The compactor also has a plurality of suction openings extending around the periphery of the piston which are connected to a vacuum source. Flexible seal flaps on the periphery of the piston engage the sides of an open-topped trash container as the piston moves into the container so that dust resulting from the compaction is removed through the suction openings to a filter box for disposal.

U.S. Pat. No. 5,012,732 to Fox describes a hydraulic trash compactor having a sanitary air filtration system for inhibiting the release of airborne particles beyond the confines of the cabinet. Motor driven fans create a negative pressure within the cabinet and a series of in-line filters are disposed in the air flow path for capturing airborne particles. The motor driven fans operate continuously at a low speed when the doors of the trash compactor or cabinet are closed and are switched to a higher speed when the doors are open. When the doors are closed, a continuous influx of air is provided through the interface between the closed doors and the side walls of the cabinet.

Finally, U.S. Pat. No. 4,407,191 to Brenner describes a weight indicator for use with a refuse compactor. Once the compacted refuse reaches a preselected weight sufficient to pivot the receptacle against the action of a spring, bellows are compressed and fluid transferred to a sight tube which indicates that the receptacle is full. Weight measurement using this system, however, will be influenced by the spatial distribution of the trash since the weight is detected based on a lever action about a fulcrum.

The prior art devices all have various deficiencies which make them undesirable for the routine disposal of bio-hazardous waste.

SUMMARY OF THE INVENTION

In view of the foregoing, it is an object of the present invention to overcome the drawbacks of the prior art.

Specifically, it is an object of the present invention to provide a bio-hazardous waste compactor with a sealed compartment to hold a trash container in which bio-hazardous waste is compacted in disposable bags. The sealed compartment is maintained at a negative gauge pressure to prevent the escape of airborne pathogens or the aerosoling of liquids. This negative gauge pressure is maintained by a venting system which consists of air ducts, a fan, an air filter and a backdraft damper. Noise is controlled by venting the filtered air through a muffler.

It is another object of the present invention to provide a bio-hazardous waste compactor which safely compacts waste to a size and weight most efficient for disposing of waste. A built in set of scales alerts the medical facility that the waste in the compactor has reached the required weight. The weight is shown on a display located on the control panel. The bag of the compactor is then removed and placed into a box for shipping to a waste disposal company.

It is a further object of the present invention to provide a sealed compartment which is designed so that a pan is formed in the lower portion of the sealed compartment which will contain any liquid that is spilled into the sealed compartment. A drain is located at the bottom of the sealed compartment to allow spilled liquids to be easily removed from the compartment.

It is another object of the present invention to provide an apparatus wherein sanitation is maintained by the use of ultraviolet lights which are turned on for predetermined periods, such as thirty minutes, to kill infectious bacteria in the sealed compartment. The air filter is also part of the sanitation system of the compactor because it prevents bacteria from leaving the sealed compartment and becoming airborne. The sealed compartment also is equipped with bushings and protective sleeves to prevent bacteria from leaking through the compacting apparatus.

It is still another object of the present invention to provide an apparatus whereby the inside of the sealed compartment may be cleaned with disinfecting liquid solution. The disinfecting solution is then drained through the drain located in the bottom of the sealed compartment. A manual override of the compactor motor allows the compactor boot to be extended with the door open so that the compactor boot and associated protective sleeves may also be cleaned.

It is a further object of the present invention to provide a container for lining a receptacle in a bio-hazardous trash compactor having an outer non-porous layer and a highly absorbent polymer layer containing a biocide layered within the outer non-porous layer. A porous layer can be provided on the interior of the highly absorbent polymer layer.

In a hospital or any medical facility with its own incinerator, the compactor will save the facility time and money by safely compacting bio-hazardous waste, thus reducing the labor needed to transport the waste to the incinerator. The compactor makes it safer and more economical to collect and handle a potentially harmful material.

DESCRIPTION OF THE DRAWING FIGURES

DESCRIPTION OF THE PREFERRED EMBODIMENT

Figure 1:
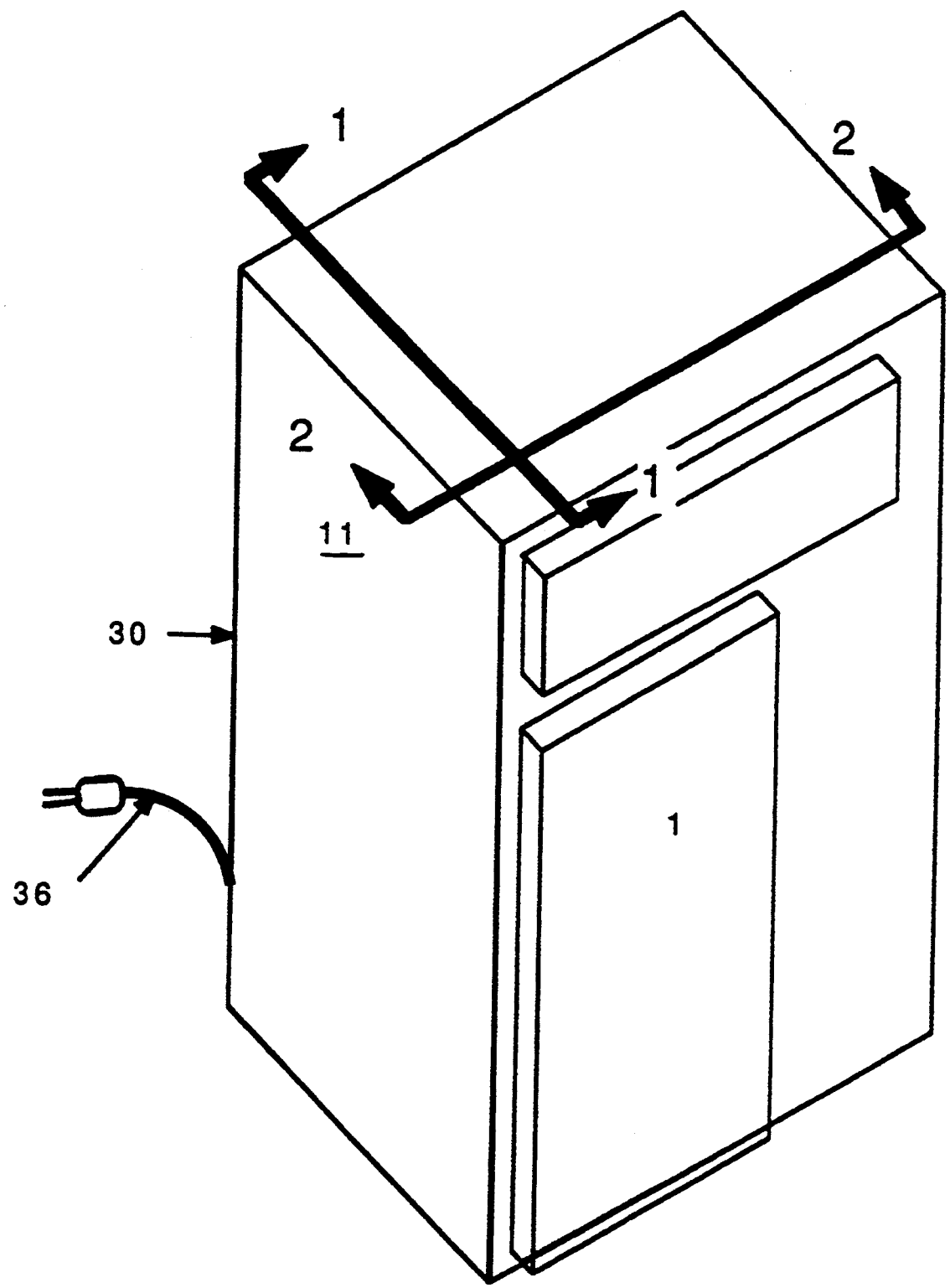
FIG. 1 is a perspective view of the compactor according to one embodiment of the present invention.
Figure 2:
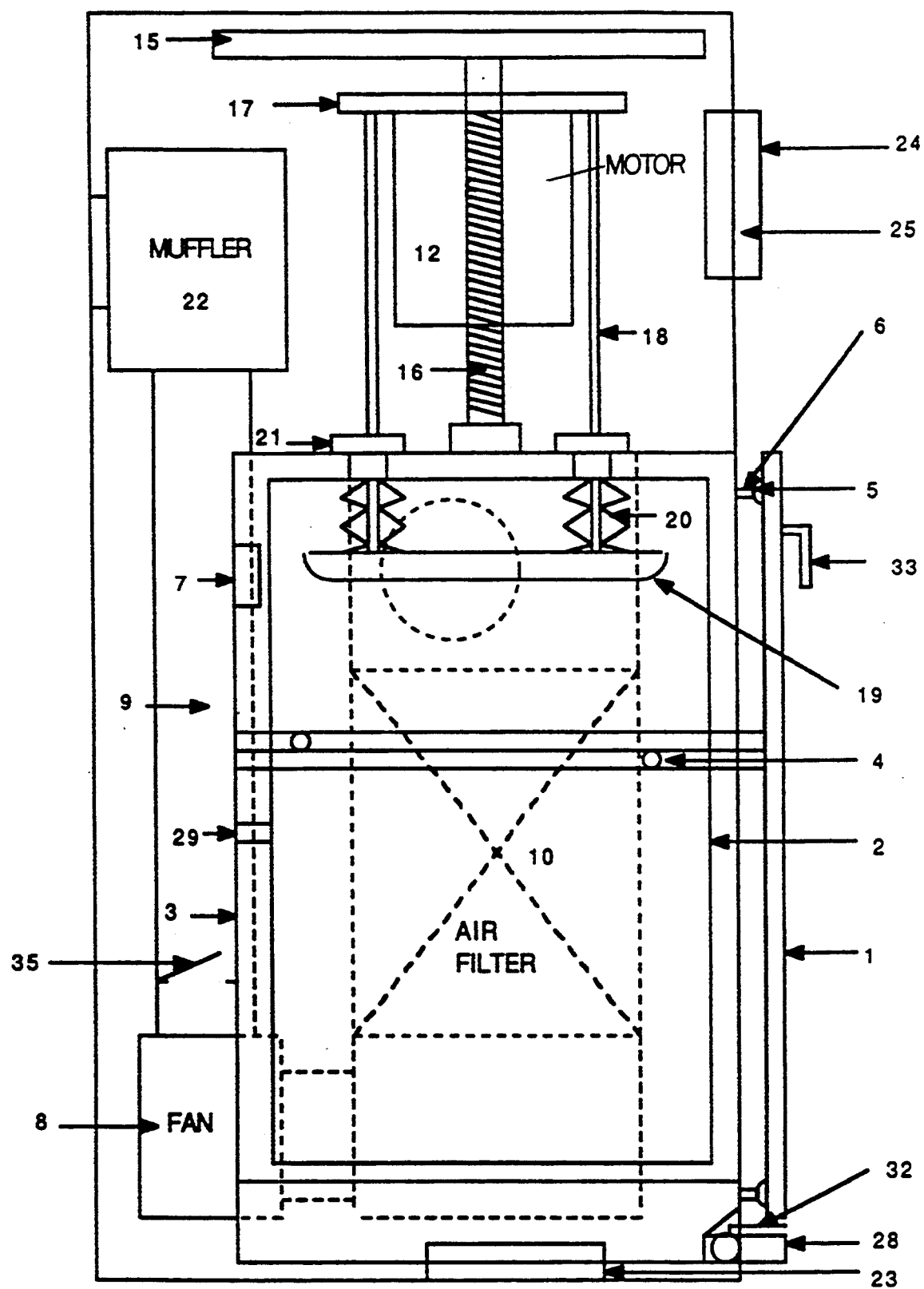
FIG. 2 is a sectional view taken along line 1—1 of the embodiment shown in FIG. 1.
Figure 3:
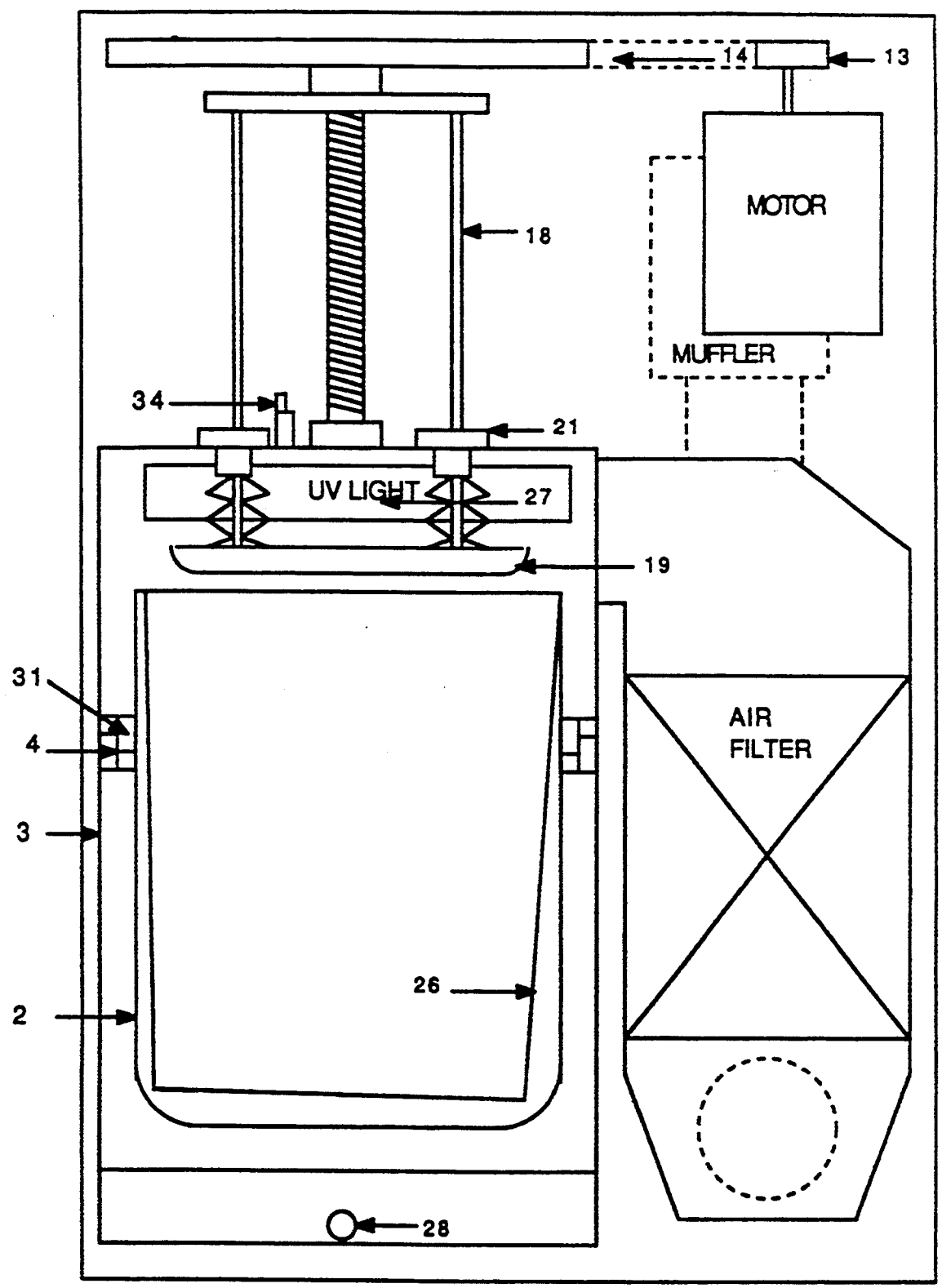
FIG. 3 is a sectional view taken along line 2—2 of the embodiment shown in FIG. 1.

Referring initially to FIGS. 1-3, the compactor (11) is housed within a metal box (30). The interior is accessible through a door (1) which covers an opening in a sealed compartment (3). A sealed compartment (3) contains a trash receptacle (2) mounted on a rack (31) on rollers (4) which allows the trash receptacle (2) to be detachably supported and reciprocally moved into and out of the opening in the sealed compartment (3).

The door (1) is opened by releasing a latch (33) which initially relieves negative air pressure in the sealed compartment (3). The door (1) is then opened and the rack (31) is withdrawn from the sealed compartment (3) by means of rollers (4) to allow the compactor bag (26) to be placed into or removed from the trash receptacle (2).

Figure 4:
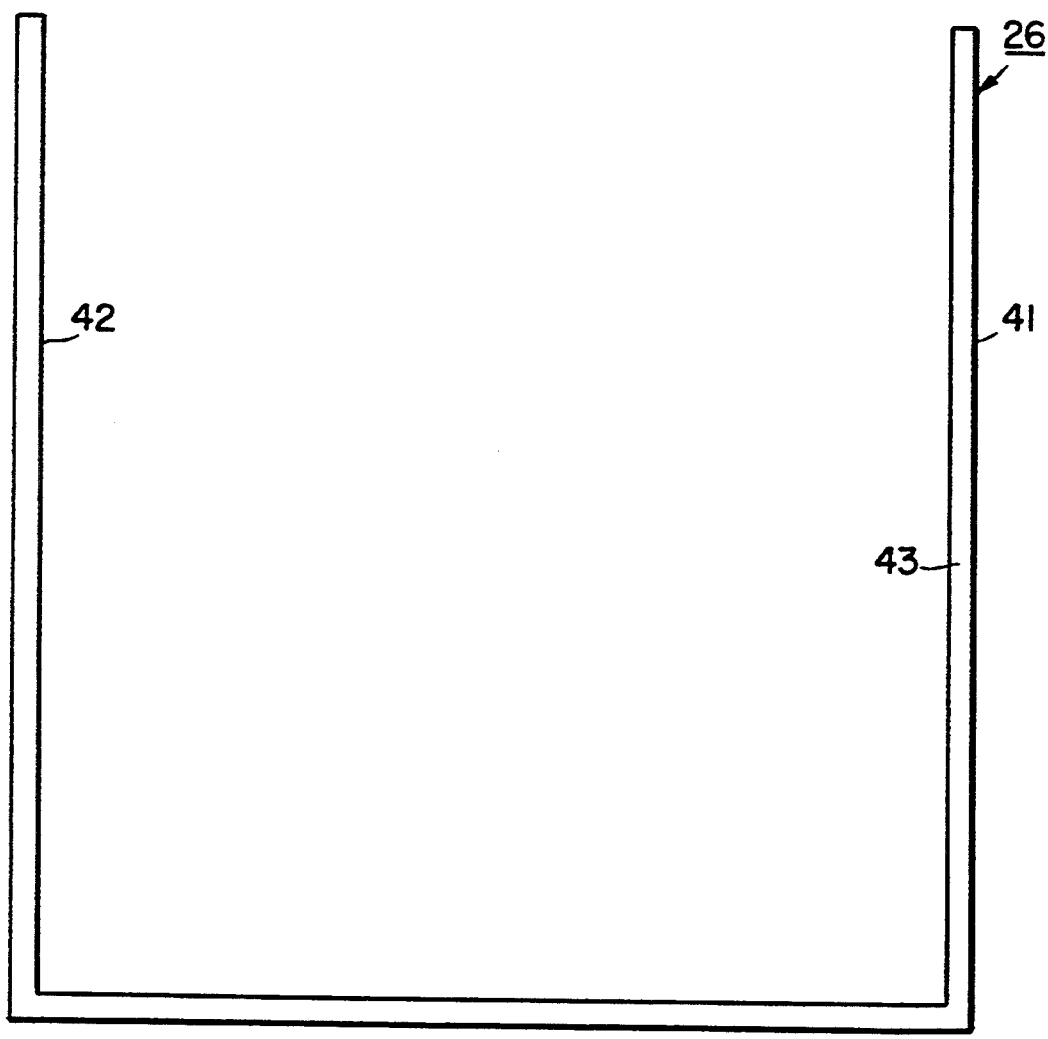
FIG. 4 is a sectional view of a bio-hazardous waste compactor bag according to one embodiment of the present invention.

As shown in FIG. 4, the bio-hazardous waste compactor bag (26) is a disposable container designed to fit into the trash container (2) of trash compactor (11). An outer non-porous layer (41) of the bag (26) can be made from a suitable heavy duty plastic and is colored red to comply with the regulatory requirements of hospitals. An inner porous layer (42) of the bag (26) can be made of porous material, such as paper. A super-absorbent layer (43), such as that found in disposable diapers, containing a biocide, which inhibits the growth of or kills the microorganisms, is placed between the outer non-porous layer (41) and inner porous layer (42). It is believed that a suitable biocide is a NALCON brand preservative available from NALCO Chemical, No. 763, used at a 500 ppm strength. When bio-hazardous waste is placed in the bag (26) for compaction, any liquid present in the waste material passes through the inner layer (41) and is absorbed by the polymer layer (43) where the liquid is disinfected by the biocide. Once the bag (26) is full, it is removed from the compactor and disposed of by incineration.

Referring back to FIGS. 1-3, biomedical waste is then put into the compactor bag (26) in trash receptacle (2). The trash receptacle (2) is then moved into the sealed compartment (3) by means of rollers (4) and rack (31). Next, the door (1) is moved to a closed position where complementary sealing members (i.e., door seals (5) and case lips (6)) are engaged to ensure an airtight seal.

When the trash receptacle (.2) is received into the sealed compartment (3), proximity switch (29) is depressed, and a negative gauge pressure is provided as described below. A compactor motor (12), which is powered by standard 110v ac current, is then turned on which drives a small pulley (13). The small pulley (13), in turn, drives pulley belt (14) in a circular motion which simultaneously drives large pulley (15). The large pulley (15) turns screw shaft (16) which lowers a compaction assembly which includes plate (17) connected to guide posts (18) which, in turn, extend into the sealed compartment (3) where they are connected to a compaction boot (19). As the compaction boot (19) moves down, the trash in the trash receptacle (2) is compacted. Once the compaction boot (19) reaches a point of refusal, or when a bottom limit switch (34) is tripped, the compactor motor (12) reverses and the compaction boot (19) is retracted. Thus, the compaction assembly allows the compaction boot (19) to be reciprocally moved into and out of the trash receptacle (2). During the movement of the compaction assembly, protective sleeves (20) and guide post bushings (21) act to seal the points at which the compaction assembly enters the sealed compartment (3), preventing the escape of pollutants from the sealed container (3).

As the compaction is taking place, a fan (8), which is powered by a 110v ac current, transports atmosphere from the sealed compartment (3) and maintains negative gauge pressure therein by pulling air through air filter (10) and pushing air through duct system (9), backdraft damper (35), and muffler (22). The muffler (22) reduces the sounds made while operating. This atmosphere removal system may be engaged at any time by pressure transducer (7) when it senses a loss of negative gauge pressure. When a sudden increase in air pressure is sensed, a higher stage speed is demanded of the fan (8). When the fan (8) is not running, backdraft damper (35) closes to prevent the loss of negative gauge pressure.

Once the compaction cycle is complete, the unit automatically measures the weight of the waste using a scale (23) provided in the sealed compartment (3). A display (24) on control panel (25) displays the weight of the waste. When the desired weight is obtained, the door (1) is opened and the trash receptacle (2) is withdrawn from the sealed compartment(3) via rollers (4) to allow the waste contained in the compactor bag (26) to be removed for disposal.

When the compactor (11) is between cycles, ultraviolet lamps (27) are turned on for thirty minute cycles to further improve sterilization. The ultraviolet lamps (27) destroy vegetative pathogenic bacteria that are exposed to the ultraviolet light.

After the waste is removed in the compactor bags (26), the operator can override the compaction cycle and extend the guide post (18) and protective sleeves (20). The inside of the sealed compartment (3) can then be cleaned by opening the door (1) and spraying the inside of the sealed compartment (3), the extended sleeves (20), and the compactor boot (19) with a disinfectant solution. The liquid cleaner may be removed from the sealed compartment through a drain (28) which is equipped with a valve (32). If there is a spillage of fluids into the sealed compartment (3) during the compaction cycle, a pan formed in the lower portion of the sealed compartment (3) would act as a sump, thus containing the fluid and preventing its spillage upon opening the door (1). This fluid may then be removed through drain (28).

While the preferred embodiments of the present invention have been described, it should be understood that various changes, adaptions and modifications may be made therein without departing from the spirit of the invention.

I claim:

1. A bio-hazardous waste compactor comprising:
    a sealable compartment having an opening;
    open-ended receptacle means for receiving bio-hazardous waste;
    reciprocal support means mounted within said sealable compartment for detachably supporting and reciprocally moving said open-ended receptacle means into and out of said sealable compartment through said opening;
    a compaction boot movable into and out of said open-ended receptacle means;
    reciprocating means extending into said sealable compartment for reciprocally moving said compaction boot into and out of said open-ended receptacle means;
    cover means for covering said opening when said open-ended receptacle means is moved into said sealable compartment;
    first sealing means disposed between said sealable compartment and said cover means for providing an airtight seal;
    second sealing means provided where said reciprocating means extends into said sealable compartment, said second sealing means further ensuring said airtight seal; and
    means in fluid communication with said sealable compartment for creating a condition of negative gauge pressure within said sealable compartment while said cover means and said first and second sealing means prevent replacement of the atmosphere within said sealable compartment.

2. The bio-hazardous waste compactor of claim 1, wherein said means for creating a condition of negative gauge pressure comprises an atmosphere removal system in communication with an interior of said sealable compartment, said atmosphere removal system comprising:
    means for transporting atmosphere from said sealable compartment;
    filter means in fluid communication with the sealable compartment for removing bacteria and other particles from said atmosphere;
    muffler means in fluid communication with said sealable compartment for reducing noise produced by said atmosphere removal system; and
    damper means in fluid communication with said sealable compartment for preventing a backdraft of said atmosphere when said means for transporting atmosphere stops, said damper means thereby maintaining a condition of negative gauge pressure in said sealable compartment.

3. The bio-hazardous waste compactor of claim 1, further comprising containing means for containing fluids spilled in said sealable compartment and fluids used to clean said sealable compartment, said containing means comprising:
    a sump portion provided in a bottom of said sealable compartment for collecting said fluids; and
    a valve means for selectively draining said fluids through a drain associated with said sump portion without opening said cover means.

4. The bio-hazardous waste compactor of claim 1, further comprising ultraviolet sterilization means provided in said sealable compartment for destroying vegetative pathogenic bacteria.

5. The bio-hazardous waste compactor of claim 1, further comprising means located beneath said open-ended receptacle for measuring a weight of said bio-hazardous waste in said open-ended receptacle when said open-ended receptacle means is moved into said sealable compartment and said cover means is covering said opening.

6. The bio-hazardous waste compactor of claim 1, further comprising response means located on a rear wall of the sealable compartment which is opposite said opening, said response means being activated when said open-ended receptacle means is moved into said sealable compartment and said opening is covered, and wherein said reciprocating means is responsive to said response means when said response means is activated.

7. The bio-hazardous waste compactor of claim 6, further comprising means operatively connected with said reciprocating means for overriding said reciprocating means when said receptacle is not disposed in the sealable compartment to allow reciprocation of said compaction boot when said response means are not activated, allowing said compaction boot and a portion of said reciprocating means extending into said sealable compartment to be cleaned.

8. The bio-hazardous waste compactor of claim 1, further comprising disposable container means received in said open-ended receptacle means for convenient removal of said bio-hazardous waste from said open-ended receptacle means, said disposable container means comprising:
    an outer non-porous layer; and
    a highly absorbent polymer layer disposed within said outer non-porous layer.

9. The bio-hazardous waste compactor of claim 8, wherein said outer non-porous layer comprises a heavy duty plastic material.

10. The bio-hazardous waste compactor of claim 8, wherein said highly absorbent polymer layer contains a biocide.

11. The bio-hazardous waste compactor of claim 8, further comprising an inner porous layer disposed within said highly absorbent polymer layer.

12. The bio-hazardous waste compactor of claim 11, wherein said inner porous layer comprises porous paper.

13. The bio-hazardous waste compactor of claim 1, further comprising a damper means, in fluid communication with said means for creating a condition of negative gauge pressure, for preventing a backdraft of atmosphere removed from said sealable compartment for maintaining a condition of negative gauge pressure in said sealable compartment.

14. A bio-hazardous waste compactor comprising:
    a sealable compartment;
    a trash receptacle disposed in said sealable compartment;
    a compaction boot movable into and out of said trash receptacle;
    reciprocating means extending into said sealable compartment for reciprocally moving said compaction boot into and out of said trash receptacle;

means in fluid communication with said sealable compartment for transporting atmosphere from said sealable compartment and providing a condition of negative gauge pressure in said sealable compartment;

filter means in fluid communication with said sealable compartment for removing bacteria and other particles from atmosphere transported from said sealable compartment; and means in fluid communication with said sealable compartment for preventing a backdraft of atmosphere transported from said sealable compartment to maintain said condition of negative gauge pressure in said sealable compartment.

15. The bio-hazardous waste compactor of claim 14, further comprising muffler means in fluid communication with said sealable compartment for reducing noise produced by said means for transporting atmosphere.

16. The bio-hazardous waste compactor of claim 14, further comprising:

a sump portion formed in a lower portion of said sealable compartment for collecting fluids; and means associated with said sump portion for draining said fluids.

17. A bio-hazardous waste compactor comprising:

a sealable compartment;

a trash receptacle disposed in said sealable compartment;

a compaction boot movable into and out of said trash receptacle;

reciprocating means extending into said sealable compartment for reciprocally moving said compaction boot into and out of said trash receptacle;

means disposed beneath said sealable compartment for measuring a weight of bio-hazardous waste in said sealable compartment when said sealable compartment is sealed;

means associated with said weight measuring means for displaying said weight of said bio-hazardous waste;

means in fluid communication with said sealable compartment for creating a condition of negative gauge pressure within said sealable compartment; and sealing means associated with said sealable compartment for preventing replacement of the atmosphere within said sealable compartment when said sealable compartment is under said condition of negative gauge pressure.

18. The bio-hazardous waste compactor of claim 17, further comprising a damper means, in fluid communication with said means for creating a condition of negative gauge pressure, for preventing a backdraft of atmosphere removed from said sealable compartment for maintaining a condition of negative gauge pressure in said sealable compartment.

19. A bio-hazardous waste compactor comprising:

a sealable compartment;

a trash receptacle disposed in said sealable compartment;

a compaction boot movable into and out of said trash receptacle;

reciprocating means extending into said sealable compartment for reciprocally moving said compaction boot into and out of said trash receptacle;

means operatively connected with said reciprocating means for overriding said reciprocating means when said receptacle is not disposed in the sealable compartment to allow reciprocation of said compaction boot when said trash receptacle is not disposed in said sealable compartment; and means in fluid communication with said sealable compartment for creating a condition of negative gauge pressure within said sealable compartment; and sealing means associated with said sealable compartment for preventing replacement of the atmosphere within said sealable compartment when said sealable compartment is under said condition of negative gauge pressure.

20. The bio-hazardous waste compactor of claim 19, further comprising a damper means, in fluid communication with said means for creating a condition of negative gauge pressure, for preventing a backdraft of atmosphere removed from said sealable compartment for maintaining a condition of negative gauge pressure in said sealable compartment.

21. A bio-hazardous waste compactor comprising:

a sealable compartment;

a trash receptacle disposed in said sealable compartment;

a compaction boot movable into and out of said trash receptacle;

reciprocating means extending into said sealable compartment for reciprocally moving said compaction boot into and out of said trash receptacle;

ultraviolet lights disposed in said sealable compartment for destroying infectious bacteria in said sealable compartment; and means in fluid communication with said sealable compartment for creating a condition of negative gauge pressure within said sealable compartment; and sealing means associated with said sealable compartment for preventing replacement of the atmosphere-within said sealable compartment when said sealable compartment is under said condition of negative gauge pressure.

22. The bio-hazardous waste compactor of claim 21, further comprising a damper means, in fluid communication with said means for creating a condition of negative gauge pressure, for preventing a backdraft of atmosphere removed from said sealable compartment for maintaining a condition of negative gauge pressure in said sealable compartment.

* * * * *